United States Patent [19]
Hiraoka et al.

[11] Patent Number: 5,615,730
[45] Date of Patent: Apr. 1, 1997

[54] METHODS FOR INSPECTING THE CONTENT OF STRUCTURE MODIFYING ADDITIVES IN MOLTEN CAST IRON AND CHILLING TENDENCY OF FLAKY GRAPHITE CAST IRON

[75] Inventors: Hidetaka Hiraoka; Mayuki Morinaka; Yasushi Kubota, all of Shizuoka, Japan

[73] Assignee: Nippon Sublance Probe Engineering Ltd., Japan

[21] Appl. No.: 320,420

[22] Filed: Oct. 5, 1994

[30] Foreign Application Priority Data

Oct. 15, 1993 [JP] Japan .................................. 5-280664

[51] Int. Cl.⁶ .......................... B22D 46/00; B22D 27/00
[52] U.S. Cl. ....................... 164/4.1; 164/57.1; 164/58.1
[58] Field of Search .................................. 164/4.1, 57.1, 164/58.1, 150.1, 151.4

[56] References Cited

U.S. PATENT DOCUMENTS

| | | | |
|---|---|---|---|
| 2,250,488 | 3/1927 | Lorig et al. | 164/58.1 |
| 4,029,140 | 6/1977 | Simmons | 164/72 |
| 4,667,725 | 5/1987 | Backerud | 164/150.1 |
| 4,696,337 | 9/1987 | Grochal et al. | 164/151.4 |
| 5,305,815 | 4/1994 | Pan Ping et al. | 164/4.1 |
| 5,328,502 | 7/1994 | Backerud | 164/57.1 |
| 5,337,799 | 8/1994 | Backerud | 164/4.1 |
| 5,373,888 | 12/1994 | Backerud | 164/4.1 |

*Primary Examiner*—Richard K. Seidel
*Assistant Examiner*—I.-H. Lin
*Attorney, Agent, or Firm*—Bierman and Muserlian

[57] ABSTRACT

Methods for inspecting the content of structure modifying additives in the molten bath of cast iron and chilling tendency of flaky graphite cast iron by means of a thermal analyzing test and a sampling vessel to be used therefor. The method consists of the steps for: obtaining a first cooling curve of the molten bath of cast iron using a first sampling vessel, obtaining a second cooling curve of the molten bath using a second sampling vessel in which small amounts of tellurium are contained, and comparing the first cooling curve with the second cooling curve.

4 Claims, 2 Drawing Sheets

METHODS FOR INSPECTING THE CONTENT OF STRUCTURE MODIFYING ADDITIVES IN MOLTEN CAST IRON AND CHILLING TENDENCY OF FLAKY GRAPHITE CAST IRON

BACKGROUND OF THE INVENTION

This invention relates to methods for inspecting the content of structure modifying additives in molten spheroidal or compacted/vermicular graphite cast iron and the chilling tendency of flaky graphite cast iron.

In manufacturing spheroidal graphite cast iron, magnesium or magnesium based alloys are added into the molten bath of cast iron.

Compacted/vermicular graphite cast iron is one of the most essential materials in industrial casting process and superior in characteristics to spheroidal graphite cast iron.

Properties of these cast irons are characterized by the shape and grain size of graphite and mechanical characteristics thereof depend upon grain size of graphite.

In manufacturing compacted/vermicular graphite cast iron, structure modifying additive which is mainly consisted of magnesium is added into the molten bath of east iron.

In order to manufacture spheroidal or compacted/vermicular graphite cast iron, compositions of the molten bath of cast iron should be inspected by thermal analyzing technique to measure the spheroidizing rate thereof. In the prior art, the molten bath of cast iron is poured into a sampling vessel made of heat resistant material in the form of a small cup with alumel-chromel thermocouple to be connected with an automatic recorder for showing a cooling curve of the sample. Eutectic and supercooling temperatures obtained from the cooling curve are analyzed for determining the spheroidizing rate of graphite.

Where structure modifying additive has not been contained or insufficient to react with the molten bath of cast iron in manufacturing spheroidal or compacted/vermicular graphite cast iron, it is impossible to determine the spheroidizing rate of graphite.

On the other hand, in manufacturing cast iron or flaky graphite cast iron without supplying any structure modifying additive, it is required to make use of chilling effect to cast iron in order to improve the mechanical characteristics. For this purpose, it is necessary to apply the technique for changing the chilling of cast iron and measuring the tendency of chilling.

OBJECTS OF THE INVENTION

It is an object of the present invention to provide a method for inspecting the content of structure modifying additives in the molten bath of spheroidal or compacted/vermicular graphite cast iron in a thermal analyzing test at the outside of the furnace.

It is a further object of the present invention to provide inspecting the chilling tendency of flaky graphite cast iron in the thermal analyzing test.

It is a still further object of the present invention to provide a sampling vessel for use of the thermal analyzing test for carrying out the above methods.

DETAILED DESCRIPTION

Heretofore it is recognized that (1) when tellurium is supplied to the molten bath of cast iron, the cast iron is converted into white pig iron, (2) tellurium is supplied to alloy cast iron of Fe-C or Fe-C-Si, the shape of graphite in the alloy cast iron changed from the state of flaky graphite to the state of eutectic graphite, and (3) tellurium is supplied to the molten bath of cast iron, the state of solidification of the molten bath of cast iron is changed to metastable state.

In view of the foregoing, according to the method of the present invention, the molten bath of cast iron is poured into a well-known standard sampling vessel with a thermocouple for use in obtaining a cooling curve of the molten bath of cast iron and at the same time the molten bath of cast iron is poured into other sampling vessel which is the same as the first-mentioned vessel in construction but small amounts of tellurium are contained therein. Cooling curves obtained from the molten bath of cast iron in these sampling vessels are compared with each other and the presence of structure modifying additive in the molten bath of cast iron is detected.

Hereinafter the sampling vessel in which tellurium is not contained is referred to as a "first sampling vessel" and the sampling vessel containing tellurium is referred to as a "second sampling vessel", respectively.

Figure 1:
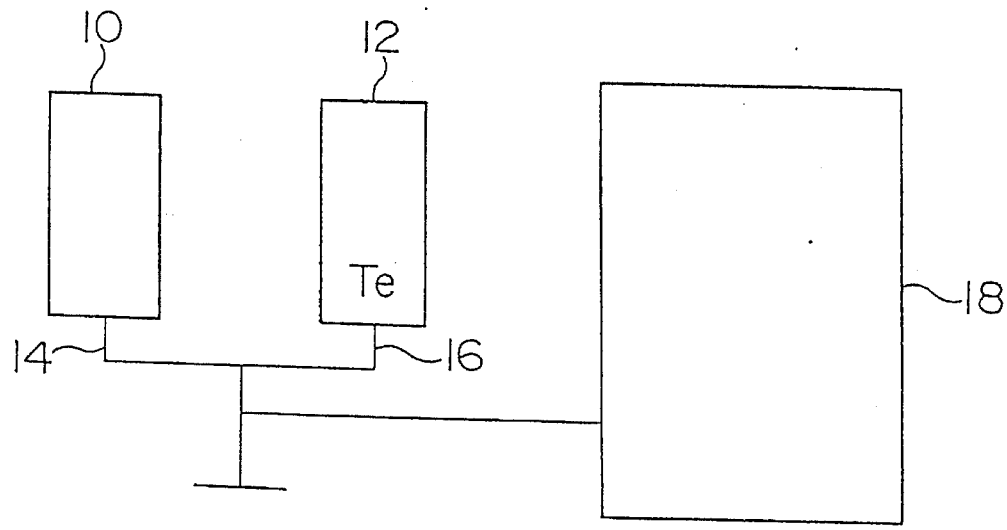
FIG. 1 is a schematic illustration of a first sampling vessel, a second sampling vessel containing tellurium (Te) and a cooling curve recorder connected to these sampling vessels for carrying out the method of the present invention.

According to the method of the present invention, for the purpose of attaining the above objects, as shown in FIG. 1, a lead wire 14 of a thermocouple (not shown) of the first sampling vessel 10 and a lead wire 16 of a thermocouple (not shown) of the second sampling vessel 12 are connected with a well-known conventional cooling curve meter 18. In prior to pour molten bath of cast iron, small amounts of tellurium are placed in the second sampling vessel 12.

The first sampling vessel 10 in which tellurium is not contained is used for inspecting spheroidizing rate of spheroidal or compacted/vermicular graphite cast iron. When the molten bath of flaky graphite cast iron is poured in the second sampling vessel 12 in which tellurium is contained, it will be solidified into white pig iron under metastable state and its eutectic supercooling temperature will not be given in its thermal analyzing.

On the other hand, if the modifying additives are contained in the molten bath of cast iron. it will be solidified in a graphite phase, and shows eutectic supercooling. Consequently, by using the second sample vessel 12 containing tellurium, it is possible to find out that the graphite in the molten bath of cast iron is flaky, compacted/vermicular or spheroidal state.

Figure 2:
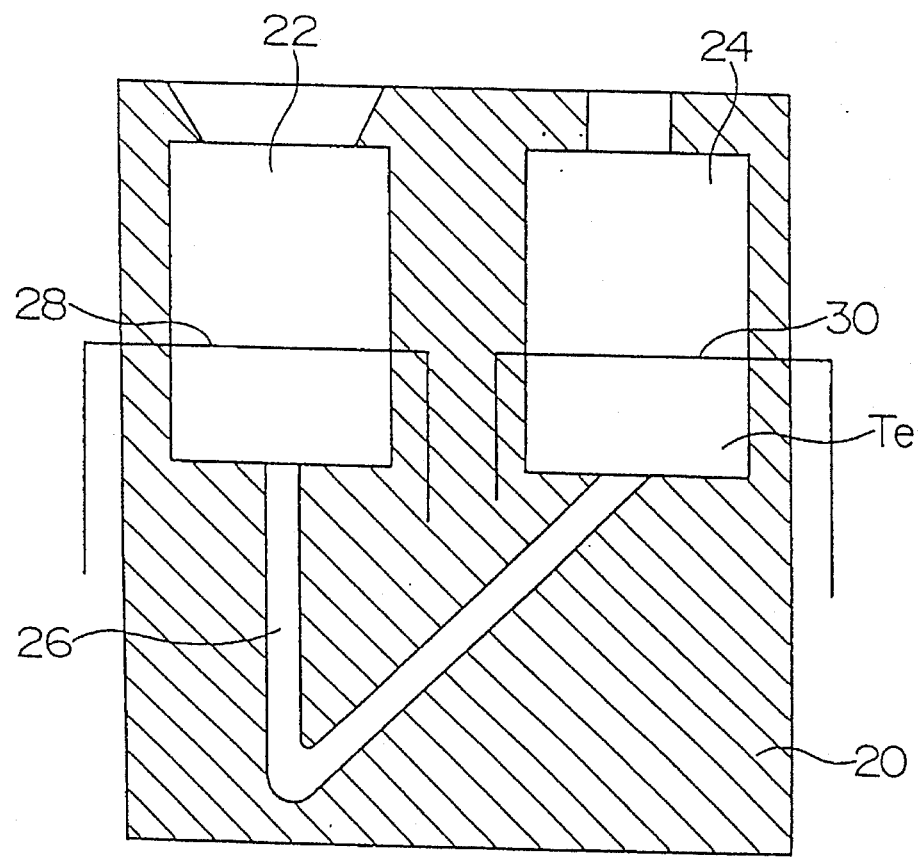
FIG. 2 is a schematic sectional view of a combined sampling vessel for carrying out the method of the present invention.

The method of the present invention can be carried out by using a single sampling vessel, as shown in FIG. 2, instead of the above-mentioned first and second sampling vessels 10 and 12.

According to the present invention, a sampling vessel 20 to be used for carrying out the above methods consists of a first cavity 22 and a second cavity 24 formed in a single block 20 of heat resisting material. Small amounts of tellurium (Te) are placed into the second cavity 24. The bottom of the first cavity 22 is connected with the bottom of the second cavity 24 by means of a V-shaped molten metal passage 26 and each of the cavities 22 and 24 is provided with a thermocouple 28 or 30 to be connected to a recording apparatus 18.

When the molten bath of cast iron is poured into the first cavity 22, it will flow into the second cavity 24 in which tellurium is contained passing through the V-shaped molten metal passage 28. The tellurium in the second cavity 24 will be prevented from the reaction with the molten bath poured into the first cavity 22, because the tellurium in the second cavity 24 cannot be entered into the first cavity 22 from the second cavity 24 through the V-shaped passage 26.

[Example for Inspecting the Content of Additives]

Pig iron and steel scraps are combined and melted by means of a high frequency electric induction furnace and prepared 20 Kg of molten bath of cast iron carbon equivalent (CE) of which was 4.4-4.0.

1 Kg of the above molten bath is transferred into a graphite crucible in which structure modifying additives are contained at a temperature of 1550° C. After the reaction of the molten bath with the additives has been completed, the portion of the molten bath is poured into the above-mentioned first sampling vessel 10 or the first cavity 22 and the second sampling vessel 12 or the second cavity 24, respectively. The cooling curves obtained from the first and second sampling vessels 10, 12 or the first and second cavities 22, 24 are compared with each other the results of which are shown in Table I.

TABLE I

| Condition of Bath | Kinds of Vessels or Cavities | Temperature of Eutectic Supercooling (°C.) | Spherodizing Rate (%) |
|---|---|---|---|
| No additive | Containing Te | 0 | |
| | No Te | 8 | flake |
| CV additive (1) | Containing Te | 11 | |
| | No Te | 21 | 38 |
| CV additive (2) | Containing Te | 2 | |
| | No Te | 11 | 70 |
| Spheroidizing additive | Containing Te | 5 | |
| | No Te | 2 | 82 |

As clear from Table 1, where no structure modifying additive is contained in the molten bath of cast iron, a microstructure of cast iron obtained from the molten bath of cast iron in the first sampling vessel 10 or the first cavity 22 is in the state of flaky graphite cast iron. On the other hand, a microstructure of cast iron obtained from the molten bath of cast iron in the second sampling vessel 12 or the second cavity 24 in which small amounts of tellurium are contained is converted into the state of white pig iron.

Where structure modifying additive for compacted/vermicular graphite (CV additive) is contained in the molten bath of cast iron, the cast iron obtained from the first sampling vessel 10 or the first cavity 22 is in the form of compacted/vermicular graphite, a spheroidizing rate of which is 38%. On the other hand, the cast iron obtained from the second sampling vessel 12 or the second cavity 24 is substantially converted into the state of flaky graphite cast iron. From the above fact, it is recognized that tellurium is the element for preventing the graphite in cast iron from converting it into spheroidal state.

If the amounts of tellurium to be added to the sampling vessel are less than 0.05% by weight with respect to the molten bath of cast iron, the molten bath in which structure modifying additive is not contained may not be converted into white cast iron. On the other hand, if more than 0.3% by weight of tellurium is added to the molten bath of cast iron, the molten bath of cast iron will be converted into while cast iron, even if structure modifying additive is added to the molten bath. Consequently, it is preferable that the amount of tellurium to be added to the molten bath of cast iron is about 0.05 through 0.3% by weight.

[Method for Inspecting the Chilling Tendency of Cast Iron]

According to the present invention, the method for inspecting the chilling tendency of flaky graphite cast iron at the outside of the furnace consists of steps for (1) obtaining the cooling curve of stable eutectic solidification of the sample of the molten bath of cast iron in which no additive is contained; (2) obtaining the cooling curve of metastable eutectic solidification of the above molten bath by adding very small amounts of tellurium; and (3) comparing the cooling curve of stable eutectic solidification with the cooling curve of metastable eutectic solidification for determining the tendency of chilling of flaky graphite cast iron.

To carrying out the above method, 20 kg of cast iron of carbon equivalent (CE) value 3.5 was melted by means of a high frequency electric induction furnace, the molten bath obtained was poured into the above-mentioned first sampling vessel 10 or the first cavity 22 and at the same time the above molten bath was poured into the second sampling vessel 12 or the second cavity 24 containing 0.1% by weight of tellurium.

By changing the quantity of Fe-Si, chilling of cast iron had been adjusted. The depth of chill was measured by using a standard chill plate, the results of which are shown in Table II.

Figure 3:
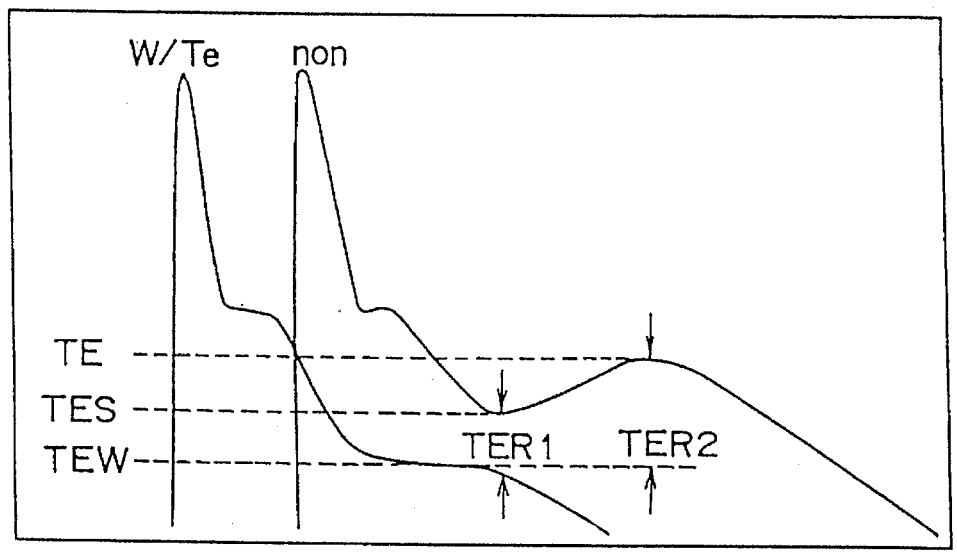
FIG. 3 is a diagram for showing a range of eutectic temperature of the molten flake cast iron obtained from each of the first sampling vessel and the second sampling vessel with tellurium (Te)
Figure 4:
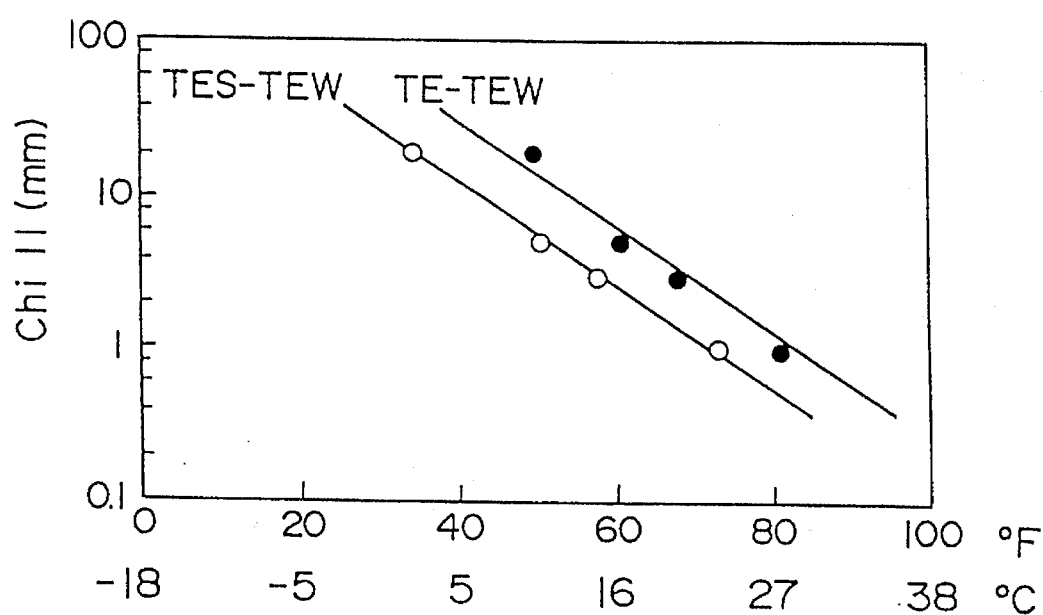
FIG. 4 is a diagram for explaining the relation between a depth of chill and an eutectic temperature of cast iron.

The cooling curve obtained from the first sampling vessel 10 or the first cavity 22 is shown in FIG. 3 at "non" and the cooling curve obtained from the second sampling vessel 12 or the second cavity 24 is shown in FIG. 3 at W/Te.

By using the detector, from the first sampling vessel 10 or the first cavity 22, a stable eutectic supercooling temperature (TES) and eutectic recalescence highest temperature (TE) were obtained, and from the second sampling vessel 12 or the second cavity 24, metastable eutectic temperature (TEW) was measured. The difference between the stable eutectic supercooling temperature (TES) and the metastable eutectic temperature (TEW) was measured as eutectic temperature range (TER1) and the difference between the eutectic recalescence highest temperature (TE) and the metastable eutectic temperature (TEW) was measured as eutectic temperature range (TER2), as shown in Table II.

TABLE II

| Fe—Si | 0 | 0.2 | 0.4 | 0.6 | 0.8 |
|---|---|---|---|---|---|
| TES | 1114 | 1135 | 1142 | 1142 | 1146 |
| TE | 1114 | 1143 | 1147 | 1148 | 1150 |
| TEW | 1116 | 1116 | 1113 | 1110 | 1105 |
| TER1 | −2 | 19 | 29 | 32 | 41 |
| TER2 | −2 | 27 | 34 | 38 | 45 |

It is recognized from the above results that if TER1 and TER2 are reduced, the depth of chilling in the cast iron will be increased, and if the two are negative, the cast iron will be converted into white cast iron.

Consequently, even though the tendency of chilling of the cast iron obtained from the molten bath thereof is unknown, it is possible to inspect it by measuring the eutectic temperature range which is the difference between the stable eutectic temperature and the metastable eutectic temperature of the molten bath of cast iron.

What is claimed is:

1. A method of determining the presence of structure modifying additives in a molten bath of cast iron comprising the steps of:

pouring a first sample of a molten bath of cast iron into a first sampling vessel having a thermocouple connected to a recording device outside of the vessel containing the molten bath;

obtaining a first eutectic supercooling curve of the sample of the molten bath of cast iron poured into the first vessel;

putting small amounts of tellurium into a second sampling vessel having a thermocouple connected to the recording device, pouring a second sample of the molten bath of cast iron with the same composition as the first sample into the second sampling vessel and obtaining a second eutectic supercooling curve of the sample of the molten bath of cast iron; and comparing the first and second supercooling curves obtained to determine the temperature difference is not zero which indicates the presence of structure modifying additives.

2. The method of claim 1 in which said amounts of tellurium to be put into the second sampling vessel are about 0.05 to about 0.3% by weight.

3. A method for inspecting the chilling tendency of flaky graphite cast iron comprising the steps of:

pouring a sample of a molten bath of flaky graphite cast iron into a first sampling vessel having a thermocouple connected to a recording device outside of the vessel containing the molten bath;

obtaining a stable eutectic supercooling curve of the molten bath of flaky graphite cast iron poured into the first vessel;

determining a first supercooling temperature from the stable eutectic supercooling curve;

putting a small amount of tellurium into a second sampling vessel having a thermocouple connected to the recording device, obtaining a metastable eutectic supercooling curve of the molten bath of cast iron poured into the second sampling vessel;

determining a second supercooling temperature from the metastable eutectic supercooling curve;

measuring the difference between the first supercooling temperature and the second supercooling temperature.

4. The method of claim 3 in which said amounts of tellurium to be put into the second sampling vessel are about 0.05 to about 0.3% by weight.

* * * * *